United States Patent [19]

Mori

[11] Patent Number: 4,630,202
[45] Date of Patent: Dec. 16, 1986

[54] COMPUTERIZED TOMOGRAPHIC APPARATUS UTILIZING A RADIATION SOURCE

[75] Inventor: Issei Mori, Tochigi, Japan

[73] Assignee: Tokyo Shibaura Denki Kabushiki Kaisha, Kawasaki, Japan

[21] Appl. No.: 561,072

[22] Filed: Dec. 14, 1983

[30] Foreign Application Priority Data

Dec. 16, 1982 [JP] Japan .............................. 57-221349

[51] Int. Cl.$^4$ ............................................ G06F 15/42
[52] U.S. Cl. .................................. 364/414; 358/111; 378/15; 378/901
[58] Field of Search ....................... 364/400, 413–415, 364/417; 358/111; 378/4, 9, 12, 15, 901

[56] References Cited

U.S. PATENT DOCUMENTS

| | | | |
|---|---|---|---|
| 3,432,657 | 3/1969 | Slavin | 378/15 X |
| 4,052,620 | 10/1977 | Brunnett | 378/901 X |
| 4,063,792 | 12/1977 | Lodge | 339/5 L |
| 4,071,769 | 1/1978 | Brunnett et al. | 378/4 X |
| 4,135,247 | 1/1979 | Gordon et al. | 364/414 |
| 4,149,247 | 4/1979 | Pavkovich et al. | 364/414 |
| 4,158,142 | 6/1979 | Haimson | 250/445 T |
| 4,181,939 | 1/1980 | Lyons | 364/414 X |
| 4,190,772 | 2/1980 | Dinwiddie et al. | 250/445 T |
| 4,211,925 | 7/1980 | Fairbairn | 250/445 T |
| 4,253,027 | 2/1981 | Taylor et al. | 250/445 T |
| 4,259,725 | 3/1981 | Andrews et al. | 364/414 X |
| 4,282,438 | 8/1981 | Nishida et al. | 250/445 T |
| 4,309,615 | 1/1982 | Kowalski | 250/445 T |
| 4,352,021 | 9/1982 | Boyd et al. | 378/12 |
| 4,365,339 | 12/1982 | Pavkovich et al. | 378/15 |
| 4,394,737 | 7/1983 | Komaki et al. | 364/414 |
| 4,426,715 | 1/1984 | Baer et al. | 378/4 |
| 4,455,667 | 6/1984 | Schwierz et al. | 378/4 |
| 4,477,922 | 10/1984 | Liebetruth | 378/4 X |

OTHER PUBLICATIONS

Ritman et al., SPIE, vol. 173, *Application of Optical Instrumentation in Medicine VII*, "Physics and Technical Considerations in the Design of the Dynamic Spatial Reconstructor (DSR)-A High Temporal Resolution Volume Scanner", 1979, pp. 382–390.

*Primary Examiner*—Gary V. Harkcom
*Attorney, Agent, or Firm*—Finnegan, Henderson, Farabow, Garrett & Dunner

[57] ABSTRACT

In a computerized tomographic CT apparatus, X-rays penetrated from a slice of an object are computer-processed so as to reconstruct a tomographic image of the imaginary slice of the object. The CT apparatus is comprised of a table couch for supporting the object to be examined, a table couch drive control circuit for controlling a continuous transportation of the table couch along a longitudinal axis of the object, an X-ray source for irradiating fan-shaped X-rays toward the imaginary slice of the object, a detector array for detecting the fan-shaped X-rays which have penetrated throught the slice of the object. It further comprises a gantry for mounting the X-ray source and the detector array in such a manner that the X-ray source is positioned opposite from the detector array with respect to the slice of the object and for performing a relative movement between the X-ray source and the detector array in a plane which is perpendicular to the longitudinal axis of the object. The apparatus enables helical scanning to be effected by the continuous transportation of the table couch and the relative movement between them. A reconstruction control circuit is provided for processing the helically-scanned projection signals derived from the detector array so as to reconstruct a tomographic image of the slice of the object.

2 Claims, 9 Drawing Figures

F I G. 4
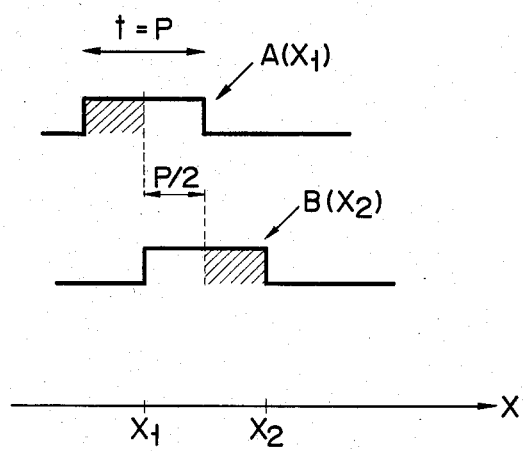
F I G. 5
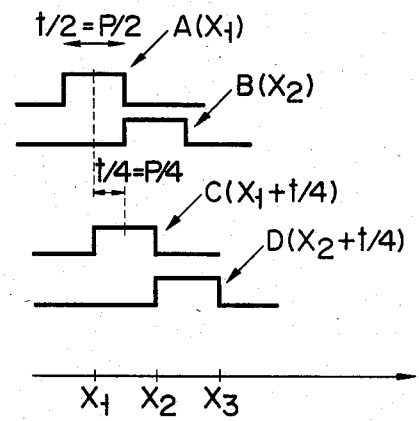
F I G. 6
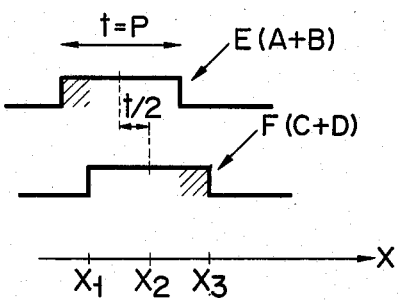

COMPUTERIZED TOMOGRAPHIC APPARATUS UTILIZING A RADIATION SOURCE

BACKGROUND OF THE INVENTION

1. Field of the Invention

This invention relates to a computerized tomographic apparatus CT for utilizing a radiation source, e.g., an X-ray source or a radioisotope.

2. Description of the Prior Art

In a conventional computerized tomographic apparatus, (although only an X-ray CT apparatus will be described in the present specification, the present invention is not limited thereto) of the type described above, when X-ray tomographic images (to be referred to as "tomographic images" hereinafter) at desired imaginary slice planes of an object to be examined such as a patient are obtained, the patient is held stationary while an X-ray tube is rotated about the longitudinal axis of the patient in a vertical section which involves the slice plane, and is intermittently projected with X-rays. When the entire projection data from every direction of the slice plane has been acquired, image reconstruction is performed on the basis of the acquired data, and thus a tomographic image of the desired slice plane is displayed on a display device.

When a plurality of tomographic images for a plurality of different slice planes is obtained in the X-ray CT apparatus as described above, the operation of the X-ray tube must be once interrupted after acquiring the entire projection data upon rotation of the X-ray tube through 180° or 360° for the first slice plane. Then, the patient is moved along the longitudinal axis such that the X-ray tube is located at a vertical section which involves the second slice plane. Then, rotation of the X-ray tube and X-ray exposure must be performed for the second slice plane as described with reference to the first slice plane.

Accordingly, when a plurality of tomographic images is required for a plurality of slice planes in a conventional X-ray CT apparatus as described above, it takes a long time to diagnose one patient, and the operation efficiency of the apparatus is lowered. In such a conventional X-ray CT apparatus, when a plurality of tomographic images is obtained for different slice planes of a patient who has been administered an X-ray contrast medium, the physiological condition of the patient changes from the time of data acquisition for the first slice plane to the time of data acquisition for the second slice plane. Thus, a plurality of tomographic images of a patient under identical physiological conditions cannot be obtained.

SUMMARY OF THE INVENTION

It is an object of the present invention to provide an X-ray CT apparatus in which the time required for mechanically transporting along the longitudinal axis a patient for whom data must be acquired and the total data acquisition time for a plurality of slice planes can be shortened.

It is a second object of the present invention to provide a CT apparatus which is capable of completing the acquisition of desired projection data within a short period of time during which the physiological condition of a patient is not substantially changed who has been administered an X-ray contrast medium for the acquisition of projection data.

Those objects and other objects of the invention will be accomplished by providing a computerized tomographic apparatus comprising:

table couch means for supporting an object to be examined;

a table couch drive control circuit for controlling a continuous transportation of the table couch means along a longitudinal axis of the object;

a radiation source for irradiating fan-shaped radiation rays toward an imaginary slice of the object;

means for detecting the radiation rays which have penetrated through the slice of the object;

means for mounting the radiation source and the detection means in such a manner that the radiation source is positioned opposite from the detection means with respect to the slice of the object and for performing a relative movement between the radiation source and the detection means in a plane which is perpendicular to the longitudinal axis of the object, whereby a helical scanning is effected by the continuous transportation of the table couch means and the relative movement between them; and a reconstruction control circuit for processing helically-scanned projection signals derived from the detection means so as to reconstruct a tomographic image of the slice of the object.

BRIEF DESCRIPTION OF THE DRAWINGS

For a better understanding of these and other objects of the present invention, reference is had to the follow detailed description of the invention to be read in conjuction with the following drawings, wherein:

FIG. 4 is an illustrative representation for explaining the distortions in the projection data;

FIGS. 5 and 6 are illustrative representations for explaining reduction of the distortions in the projection data;

DETAILED DESCRIPTION OF THE PREFERRED EMBODIMENTS

As pointed out in the preamble of the present specification, although an X-ray CT apparatus will now be described in more detail, the present invention is not, however, limited to such an X-ray CT apparatus, but also to any CT apparatus for utilizing a radiation source, or a plurality of X-ray sources for a fast scanning. Accordingly for a better understanding, the following embodiments will describe an X-ray CT apparatus employing one X-ray source.

Figure 1:
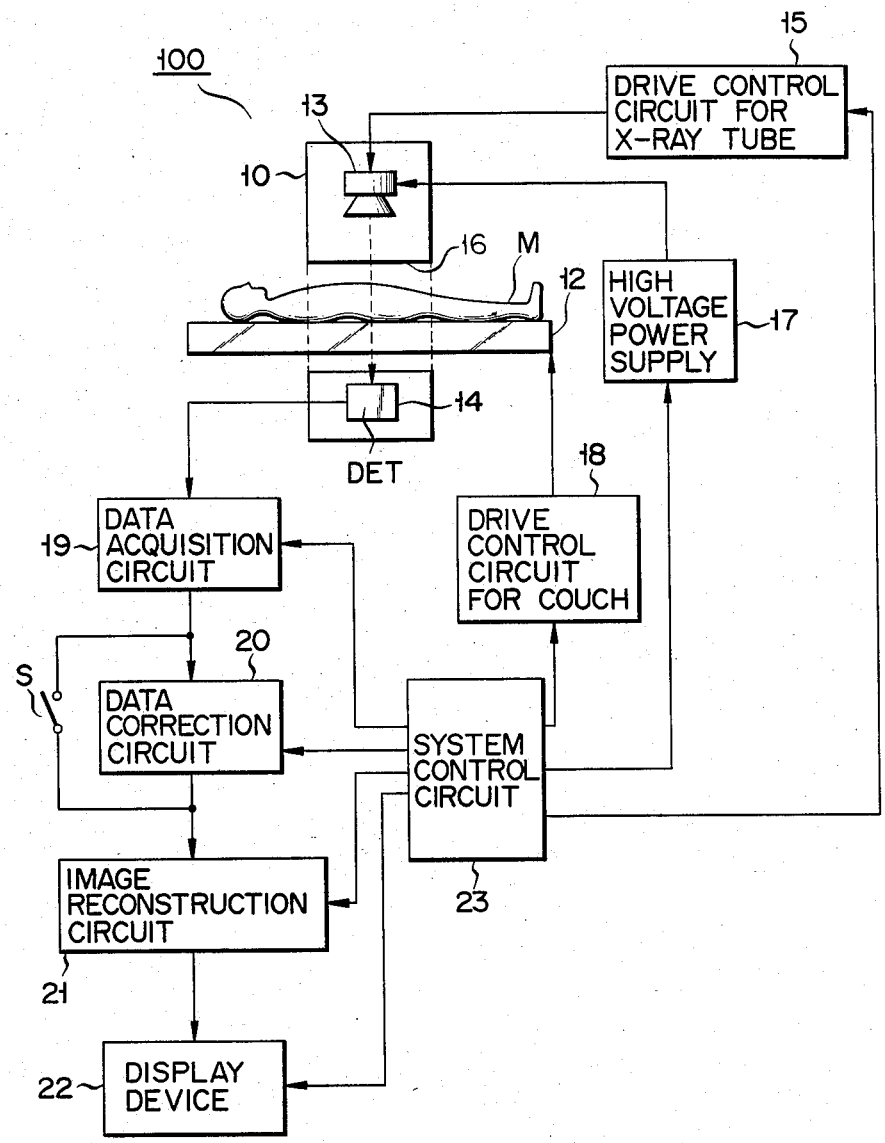
FIG. 1 shows a block diagram of a computerized tomographic apparatus according to one preferred embodiment.

FIG. 1 is a system block diagram of an X-ray CT apparatus 100 according to one preferred embodiment of the present invention. A gantry 10 has an opening 16 for inserting therethrough an object such as a patient M lying on a table couch 12. An X-ray tube 13 as an X-ray source and an X-ray detector array 14 oppose each other through the inserted patient M. X-ray radiation from the X-ray tube 13 is controlled by a high voltage power supply 17. The X-ray tube 13 is driven by a drive control circuit 15 so as to rotate around the opening 16 within the gantry 10. The X-ray detector array 14 consists of an array of a plurality of detector elements arranged along the circumferential surface of a cylindrical holder (not shown). At all times of the rotation, some of the single elements of the X-ray detector array 14 are arranged to receive X-rays which are emitted from the X-ray tube 13 and transmitted through the patient M. The table 12 can be continuously, not interruptedly moved by a drive control circuit 18 for table couch along the longitudinal axis of the patient M. A data acquisition circuit 19 acquires data obtained by the X-ray detector array 14. A data correction circuit 20 is provided for obtaining reconstruction data from the data in the data acquisition circuit 19, as will be described below. An image reconstruction circuit 21 performs image reconstruction based on the data supplied from the data correction circuit 20. A display device 22 produces a display based on the image data from the image reconstruction circuit 21. A system control circuit 23 controls all of the above-described circuits. A by-pass switch S by-passes data from the data acquisition circuit 19 into the data correction circuit 20.

In the apparatus described above, it is assumed that a fan-beam X-ray or fan-shaped X-ray FB is irradiated from the X-ray tube 13, the X-ray detector array 14 detects the fan-beam X-ray FB as a single detection unit, and the fan-beam is rotated not just by 360°, but continuously through 10 rotations or any finite numbers of rotation. Such a continuous rotation can be realized by a slip-ring system as disclosed in, e.g., U.S. Pat. No. 4,063,792, issued on Dec. 20, 1977 or an electron beam X-ray scan system as disclosed in U.S. Pat. No. 4,158,142 issued on Sept. 28, 1982. According to the feature of the invention, the patient M is continuously transported by the drive control circuit 18 for table couch while the fan-beam FB continuously rotates and data is acquired. The patient M is transported by a distance of "P" mm along the longitudinal axis thereof upon one rotation of the fan-beam. With this construction, the same effect can be realized as in the case wherein the fan-beam rotates around the patient M which is remained stationary while it is subject to parallel movement along the longitudinal axis. Consequently, the fan-beam helically rotates around the patient M and acquires data (this rotation is so-called "helical scanning"). The data obtained by the helical scanning is defined as "helically-scanned data". Accordingly, helically-scanned data can be obtained not only in a CT apparatus wherein the X-ray tube 13 alone is rotated and the X-ray detector array 14 is held stationary (fourth generation CT apparatus), but also in a CT apparatus wherein the opposing X-ray tube and X-ray detector array rotate relative to each other (third generation CT apparatus). When the positions of the helical scan X-ray source and the fan-beam are observed in a direction perpendicular to the longitudinal axis of the patient M, a sinusoidal trail "XL" having a period of "P" mm as shown in FIG. 2 is obtained.

Figure 2:
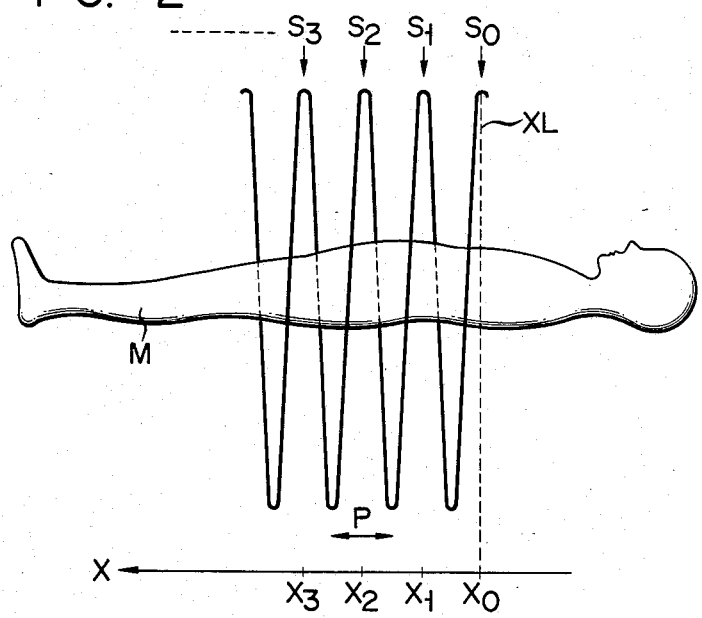
FIG. 2 is an illustrative representation for explaining the helically-scanning method which is employed in the embodiment shown in FIG. 1.
Figure 3:
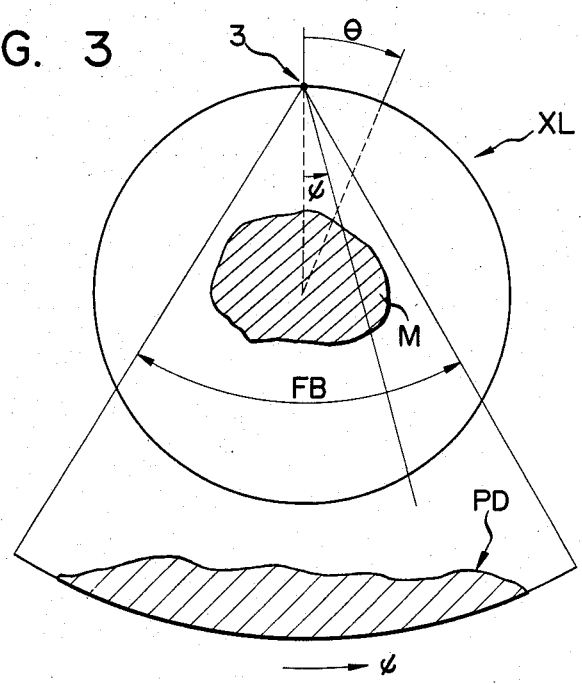
FIG. 3 is an illustrative representation for explaining the fan-beam of the embodiment shown in FIG. 1.

A method for reconstructing an image from the data obtained in this manner will now be described. Reconstruction methods include (1) a method wherein the total range of scanning is divided into small regions, i.e., voxels, and reconstruction is performed simultaneously for all these regions; and (2) a method wherein when data obtained upon rotation of the X-ray tube from a slice point $S_1$ to $S_2$ in FIG. 2 is considered, as the position of the fan-beam is approximated to be at the center between positions $X_1$ and $X_2$ along the X direction in FIG. 2, an image is reconstructed for each slice plane which is fixed at the center as it were (disclosed in, e.g., U.S. Pat. No. 4,149,247). It is also possible to take an average value of the data obtained upon two rotations of the X-ray tube from the slice point $S_1$ to $S_3$ in accordance with equation (1) below which data is considered as data corresponding to one rotation and to reconstruct an image of the slice position $X_2$ using the average value as scanning data.

$$P(\theta,\psi)=\{P_{12}(\theta,\psi)+P_{23}(\theta,\psi)\}/2 \ldots \quad (1)$$

where $\theta$ is the rotation angle of the X-ray tube 13, that is, the X-ray fan-beam FB, as shown in FIG. 3 and is 0° to 360°, $P_{12}(\theta,\psi)$ is projection data obtained when the position of the X-ray tube 13 relative to the patient M moves from the slice point $S_1$ to $S_2$ shown in FIG. 2, and $P_{23}(\theta,\psi)$ is similarly projection data obtained when the position of the X-ray tube 13 relative to the patient M moves from the slice point $S_2$ to $S_3$.

The above method can be applied when an image for one slice plane is obtained upon three rotations or more of the X-ray tube.

When a plurality of projection data are averaged, each projection data can be equally weighted to obtain an average value as explained in conjunction with equation (1). Alternatively, each projection data can be weighted by a different weighting coefficient to obtain an average value.

Furthermore, projection data obtained upon each rotation of the X-ray tube can be independently reconstructed, and a plurality of resultant images can be summed to obtain an average value, thereby obtaining the similar effect as described above.

Another embodiment of the present invention will now be described. The method of obtaining one image from data acquired during a plurality of continuous rotations provides advantages in that the artifact can be reduced in that image. In a conventional X-ray CT apparatus, the thickness of the X-ray fan-beam viewed from its side is substantially proportional to the distance from the X-ray tube, since the side view of the X-ray fan-beam is not parallel.

When the patient is examined by such a non-parallel X-ray fan-beam, the projection data includes a slightly contradictory portion for each projection angle $\theta$ (where $\theta \geq 0$), and an artifact called "a clipping effect" is caused in the case of a patient under the following condition. Assume that an examination slice of a patient is in a condition wherein a portion having a low X-ray transmission factor such as a bone is present discontinuously. When such a slice is exposed to a fan-beam at two examination positions of $\theta=0$ and $\theta=180°$, some portions of the slice are exposed to the fan-beam at only one of these two angles, thereby causing a clipping effect.

Such a clipping phenomenon will be described with reference to FIG. 4. Referring to FIG. 4, a waveform A indicates an intensity profile along the slice thickness of the X-ray fan-beam which is obtained when the X-ray tube 13 is at the slice position $S_1$ (i.e., $X=X_1$) shown in FIG. 2. The slice thickness at this time is given as "t"

mm. This means that the patient M is moved at a scanning pitch of "t" mm per rotation of the X-ray fan-beam. While the X-ray tube is rotated, the slice plane is shifted along the longitudinal axis of the patient. When at $\theta=180°$, for example, the X-ray tube is not at the initial position $X_1$ but is located at a position ($X=X_1+P/2$; a midpoint between the positions $X_1$ and $X_2$) which is advanced by P/2 therefrom. If P=t, the intensity profile and position of the X-ray fan-beam along the slice thickness direction at $\theta=180°$ are indicated by a waveform B in FIG. 4. In the waveforms of the intensity profiles A and B, the hatched regions indicate that not common portions of the patient are examined, i.e., contradictory portions. As is well known, image reconstruction is performed under the recognition that the entire projection data is obtained for the completely same slice plane of the patient. This means that the hatched regions in the waveforms of the intensity profiles A and B must cause such distortions in the resultant image, and this is applicable to the entire range of the projection angle $\theta$, not only in the just described case of $\theta=0°$ and $\theta=180°$. Accordingly, even with the data acquisition method of the former embodiment described above, the clipping phenomenon is liable to occur.

The second embodiment of the present invention solves this problem by the adoption of the following principle. When a CT image having an effective slice width of "t" mm is desirable, the patient M is continuously moved at a scanning pitch of t/2 mm per rotation of the X-ray fan-beam. The X-ray fan-beam FB is narrowed to t/2 mm by a collimator or the like. As a result of this, waveforms of the intensity profiles and positions as shown in FIG. 5 are obtained. Referring to FIG. 5, waveforms A and B indicate the intensity profiles and positions along the slice plane thickness of the X-ray fan-beam obtained when the relative position of the X-ray tube is $X=X_1$ and $X=X_2$, respectively. Waveforms of intensity profiles and positions "C" and "D" are similarly obtained for:

$X=(X_1+X_2)/2+X_1+t/4$, and $X=(X_2+X_3)/2+X_1+3t/4$, respectively.

Consequently, when an average value of the projection data is obtained as in equation (1), the waveforms of the profiles and positions E and F as shown in FIG. 6 are obtained. More specifically, waveforms E and F are obtained along the slice plane thickness for the projection data when $\theta=0°$ and $\theta=180°$. The waveform of the intensity profile E is obtained by adding the waveforms of the intensity profiles A and B and the waveform of the intensity profile F is obtained by adding the waveforms of the intensity profiles C and D, so that each of the profile waveforms E and F has an effective slice width of "t" mm. It can be understood that in these profile waveforms E and F, the hatched regions become smaller than in the case of FIG. 4. Thus, the image distortion is reduced in the case of the second embodiment compared with that in the case of the first embodiment described above.

As has been described in detail, according to the principle of the present embodiment, the data portions (hatched regions) which result in an image distortion, i.e., artifacts, can be reduced as the scanning pitch of the X-ray fan-beam is reduced.

A third embodiment of the present invention will now be described. When the helical scanning is performed in the above embodiments, the following problem may occur. When acquisition of the projection data starts at the rotation angle $\theta$ of the fan-beam being 0° and acquisition of the projection data of one image is completed at a position of $\theta$max close to the position $\theta=360°$, the obtained data significantly differ from each other, since the scanning planes deviate from each other for $P(0,\psi)$ and $P(\theta\text{max},\psi)$. In general, if there is a discontinuous deviation between adjacent data, an artifact is readily caused as compared to the case of a continuous deviation between adjoining data. To solve this problem, the computerized tomographic diagnostic apparatus according to the third embodiment of the present invention employs a data correction circuit 20 which performs the following processing. That is, the by-pass switch "S" in the circuit shown in FIG. 1 is opened so that the acquired data in the data acquisition circuit 19 is supplied through the data correction circuit 20 to the reconstruction circuit 21. The principle of the data correction circuit 20 is such that a part of the projection data for image reconstruction for one slice plane which is obtained in the initial or final stage of a given rotation of the X-ray tube is corrected by the data of another slice plane of which is taken at the same rotation angle during the immediately preceding or succeeding rotation of the X-ray tube.

Figure 7:
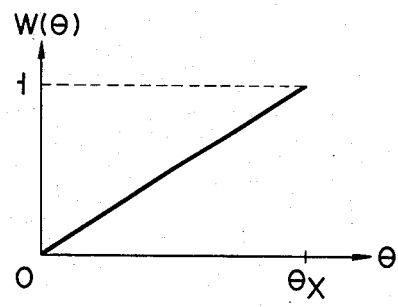
FIG. 7 is a graphic representation for the function to be used in the correction data circuit.

Consequently, the projection data which has been obtained for a rotation angle range of $\theta=0°$ to $\theta=X$ can be substituted by data $P'(\theta,\psi)$ which has been subjected to an arithmetic operation as given by equation (2) below:

$$P'(\theta,\psi)=W(\theta)\cdot P_{12}(\theta,\psi)+(1-W(\theta))\cdot P_{23}(360°+\theta,\psi) \quad (2)$$

where $\theta X$ is appropriately given in accordance with the width of the image reconstruction region and the degree of artifact, and $W(\theta)$ is a function which connects between 0 at $\theta=0°$ and 1 at $\theta=\theta X$ without any abrupt change, as shown in FIG. 7.

On the other hand, instead of such a data correction, the above-described data obtained for $\theta=\theta Y$ to $\theta$max can be alternatively substituted by data $P'(\theta,\psi)$ which has been arithmetically processed by the data corrected by the data obtained in the immediately preceding or succeeding rotation of the X-ray tube in accordance with equation (3) below:

$$P'(\theta,\psi)=W(\theta)\cdot P_{12}(\theta,\psi)+(1-W(\theta))\cdot P_{23}(\theta-360°,\psi) \quad (3)$$

where $\theta Y$ has the same meaning as that of $\theta X$ given above, and $W(\theta)$ is a function which connects between 1 at $\theta=\theta Y$ and 0 at $\theta=\theta$max without any abrupt change.

When such a data correction circuit 20 is introduced, the adjacent data can be evaluated as a continuous deviation and therefore the generation of the artifact can be reduced. In the above description, a desired single CT image was obtained for the two data corresponding to one rotation of the X-ray tube from the position $S_1$ to the position $S_2$ and corresponding to slight additional rotation angle. Moreover according to this embodiment, the data of a single image can be similarly obtained upon two rotations or three rotations together with a slight additional rotation angle.

While the present invention has been described in detail, the principle operation of each embodiment will now be summarized.

In the first embodiment, the so-called "helically-scanned data" of the slice of the object is obtained by helically-scanning the X-ray source 13 and the X-ray detector array 14 along the longitudinal axis of the object while the object is continuously transported along its longitudinal axis. A plurality of the helically-scanned data thus obtained is calculated based upon the formula (1) so as to obtain the averaged reconstruction scan data.

In the second embodiment, a plurality of the helically-scanned data is obtained by controlling the continuous transportation of the object with respect to the relative movement between the X-ray tube and the detector array so as to scan the object at a predetermined smaller scanning pitch than an effective width of the slice of the object.

In the third embodiment, one portion of the helically-scanned data which has been obtained at the beginning or the last portion of one slice data is corrected in the data correction circuit based upon formula (2) or (3) by utilizing another helically-scanned data which was obtained at the immediately preceding scanning operation or at the immediately succeeding scanning operation with respect to the same projection angle.

Figure 8:
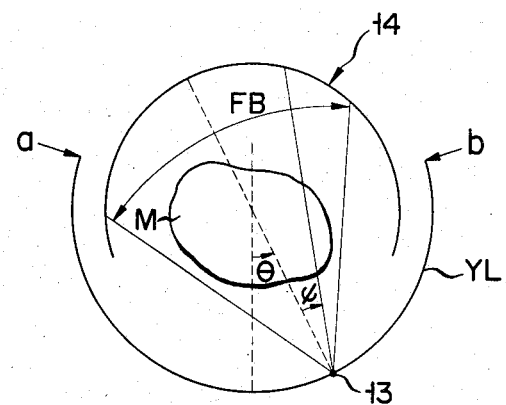
FIG. 8 is a schematic representation for explaining operations of another embodiment.
Figure 9:
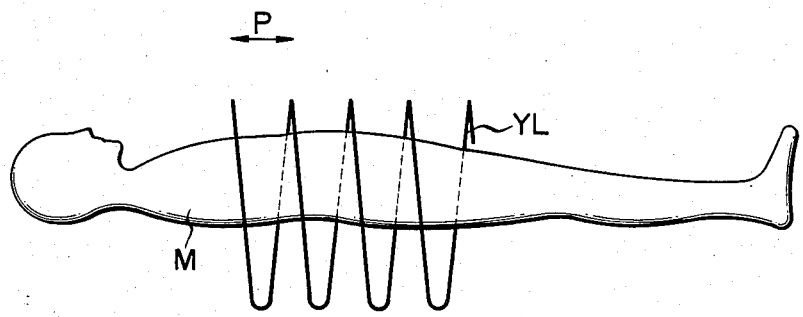
FIG. 9 is an illustrative representation for explaining the modified helically-scanned method which is employed in the embodiment shown in FIG. 8.

The present invention is not limited to the particular embodiments described above but various changes and modifications may be made within the spirit and scope of the present invention. For example, in the above embodiments, an X-ray CT apparatus is described wherein a single image is obtained from the projection data corresponding to a rotation angle range of 0° to 360°. However, the present invention can be similarly applied to an X-ray CT apparatus which performs image reconstruction from scan data corresponding to a rotation angle range of less than 360°, as shown in FIG. 8. For example, the X-ray source can be reciprocally or one way shifted at high speed on a trail "YL", and the detector array 14 can be arranged along the range of ⅔ of the entire circumference of the opening. The patient M can be continuously moved during repetitive scanning. In this case, projection data of a single image can be obtained when an X-ray source 13 moves from position "a" to position "b". The apparatus of this type can provide a continuous U-shaped scan trail as shown in FIG. 9. The data obtained in this manner can be defined as "modified helically-scanned data" in the present specification. In this case, the moving speed of the X-ray source 13 from the position "b" to the position "a" (return movement) must be extremely higher than that from the position "a" to the position "b" (in the data acquisition period). This may be realized by a known electron beam X-ray scan as in, e.g., U.S. Pat. No. 4,352,021. According to the apparatus of this embodiment, the travel time of the X-ray source 13 can be shortened. Therefore, since the slice pitch P mm can be also made extremely small, the artifact can be reduced by preparing an image of one slice plane by superposing a number of projection data utilizing equation (1) above.

In the above embodiments, the X-ray tube and the X-ray detector array are rotated relative to the patient. That is, either both the X-ray tube and the X-ray detector array are rotated (third generation CT apparatus), or the X-ray tube alone is rotated while the detector array is fixed in a given position. However, the definition of such a "relative rotation" is not limited to the above rotations. For example, an object, e.g., industrial product, may be rotated around its own longitudinal axis while the X-ray tube or detector array is fixed in predetermined positions, and simultaneously is continuously moved along this axis. It should be noted that the CT apparatus according to the invention can examine not only an object such as a patient, but also an object such as an industrial product for non-destructive examination. Furthermore, projection data can be acquired when the X-ray tube and detector array are continuously moved along the longitudinal axis of the subject while the subject is rotated therearound.

As described in the preamble, since the present invention is not limited to a CT apparatus of X-ray type, a radiation source other than the X-ray tube, e.g., a radioisotope, can be utilized, and also a plurality of X-ray sources can be utilized for the fast scanning purposes.

According to the present invention described above, there is provided an X-ray CT apparatus wherein the time required for moving the object during data acquisition can be shortened, and the total data acquisition time for a plurality of slice planes can also be shortened, so that the examination time of the object can be reduced.

What is claimed is:

1. A computerized tomographic scanner for obtaining images of multi-planar slices of an object comprising:
   a radiation source for continuously rotating fan-shaped radiation rays irradiated toward a slice of the object;
   radiation detector means having a plurality of elements for converting said radiation rays into an electrical signal proportional to an intensity thereof, and for detecting said fan-shaped radiation rays, penetrated through the slice of the object by said elements disposed opposite to said radiation source with respect to the object, to produce projection data representative of the profile of said intensities of said fan-shaped radiation rays penetrated through the slice at a rotation angle of said fan-shaped radiation rays;
   object support means for continuously transporting said object so that said fan-shaped rays successively intersect said multi-planar slices of said object whereby helical scanning is effected by the continuous transportation of said object support means and movement between said radiation source and said radiation detector means;
   correcting means for receiving said projection data for rotation angles larger than 360°, and smoothing said projection data of corresponding rotation angles for different scan slices to produce corrected projection data including smoother projection data for said corresponding rotation angles; and
   reconstruct means for reconstructing said image of the slice from said corrected projection data.

2. A computerized tomographic scanner according to claim 1, wherein said object support means continuously transports said object by the same distance as a thickness of said fan-shaped rays per rotation of said fan-shaped rays.

* * * * *